(12) United States Patent
Meikle et al.

(10) Patent No.: US 10,247,644 B2
(45) Date of Patent: Apr. 2, 2019

(54) AIR SAMPLING SYSTEM FOR A LOW-TEMPERATURE SPACE THAT ENABLES REMOVAL OF ICE BUILD-UP WITHIN A SAMPLING CONDUIT

(71) Applicant: Xtralis Technologies Ltd., Nassau (BS)

(72) Inventors: Peter John Meikle, Mont Albert (AU); Paul Basil Leslie, Gaven (AU); John Vythoulkas, Brunswick (AU); Matthew Stephen Korsa, East Bentleigh (AU); Tawfeeq Gehad Al-Farra, East Bentleigh (AU); Ronald Knox, Mount Eliza (AU)

(73) Assignee: Garrett Thermal Systems Limited, Berkshire (GB)

( * ) Notice: Subject to any disclaimer, the term of this patent is extended or adjusted under 35 U.S.C. 154(b) by 0 days.

(21) Appl. No.: 14/768,516

(22) PCT Filed: Sep. 30, 2013

(86) PCT No.: PCT/AU2013/001121
§ 371 (c)(1),
(2) Date: Aug. 18, 2015

(87) PCT Pub. No.: WO2014/127397
PCT Pub. Date: Aug. 28, 2014

(65) Prior Publication Data
US 2016/0003714 A1  Jan. 7, 2016

(30) Foreign Application Priority Data

Feb. 19, 2013  (AU) ................................ 2013900547

(51) Int. Cl.
*B08B 9/02* (2006.01)
*G01N 1/22* (2006.01)
(Continued)

(52) U.S. Cl.
CPC ........... *G01N 1/2273* (2013.01); *B08B 9/021* (2013.01); *F16L 5/10* (2013.01); *G01N 1/2226* (2013.01);
(Continued)

(58) Field of Classification Search
CPC ........ G01N 2001/2235; G01N 1/2226; G01N 2001/2229; F16L 5/10; F16L 5/12;
(Continued)

(56) References Cited

U.S. PATENT DOCUMENTS 3,181,899 A * 5/1965 McKnight, Jr. ......... F16L 41/14
                                                    285/139.2
4,571,079 A   2/1986 Knollenberg
(Continued)

FOREIGN PATENT DOCUMENTS

CA     1 186 915 A1   5/1985
CA     1335073 C      4/1995
(Continued)

*Primary Examiner* — Justin N Olamit
(74) *Attorney, Agent, or Firm* — Boyle Fredrickson, S.C.

(57) ABSTRACT

An air sampling system for a low-temperature space is disclosed. The air sampling system includes an air sampling pipe for passing sampling air to an air sampling device, and a sampling conduit extending from the low-temperature space to outside the low-temperature space. The sampling conduit is connected to the sampling pipe. The sampling conduit is selectively accessible from outside the low-temperature space for removal of ice build-up within the sampling conduit. Also disclosed is a kit for an air sampling system. Also disclosed is a method, computing system, air-sampling device and air monitoring system that evaluates an air sampling network.

9 Claims, 9 Drawing Sheets

(51) Int. Cl.
*F16L 5/10* (2006.01)
*G08B 17/10* (2006.01)
*G08B 17/113* (2006.01)

(52) U.S. Cl.
CPC ............ *G08B 17/10* (2013.01); *G08B 17/113* (2013.01); *G01N 2001/2229* (2013.01)

(58) Field of Classification Search
CPC . F16L 41/08; F16L 41/14; F16L 47/28; F16L 55/02754; F25D 29/006; F25D 29/008
See application file for complete search history.

(56) References Cited

U.S. PATENT DOCUMENTS

| | | | |
|---|---|---|---|
| 6,427,543 B1 | 8/2002 | Torrison | |
| 6,948,391 B2* | 9/2005 | Brassell | G01N 1/2226 73/863.84 |
| 7,216,556 B2 | 5/2007 | Desrochers et al. | |
| 7,360,461 B2* | 4/2008 | Desrochers | G01N 1/22 73/863.71 |
| 7,415,901 B2* | 8/2008 | Desrochers | G01N 1/26 236/1 B |
| 7,703,344 B2* | 4/2010 | MacPherson, III | G01N 1/2247 73/863 |
| 2005/0229982 A1* | 10/2005 | Gonzales | E03F 5/101 137/590 |
| 2012/0036942 A1 | 2/2012 | Hasunuma | |

FOREIGN PATENT DOCUMENTS

| | | | |
|---|---|---|---|
| DE | 19605842 C1 | 4/1997 | |
| FR | 2664608 A1 * | 1/1992 | ............ C09D 183/04 |
| JP | H02-237687 A | 9/1990 | |
| JP | H08-313392 A | 11/1996 | |
| JP | H11-190686 A | 7/1999 | |
| JP | 2000-019082 A | 1/2000 | |
| JP | 2002088317 A * | 3/2002 | |
| JP | 2005-172682 A | 6/2005 | |
| WO | 94/05992 A1 | 3/1994 | |
| WO | 2006/049434 A1 | 5/2006 | |

* cited by examiner

AIR SAMPLING SYSTEM FOR A LOW-TEMPERATURE SPACE THAT ENABLES REMOVAL OF ICE BUILD-UP WITHIN A SAMPLING CONDUIT

RELATED APPLICATION

This application claims the benefit of Australian provisional patent application 2013900547, filed 19 Feb. 2013, which is incorporated herein by reference for all purposes.

BACKGROUND OF THE INVENTION

1. Field of the Invention

The present invention relates to an air monitoring and/or sampling for a low-temperature space. In a preferred form, although not exclusively, the invention relates to an aspirating smoke detection system for a refrigerated storage facility. However, it will be understood that the invention may have application to other types of air monitoring systems e.g. gas detection systems, aerosol detection of biological material or other types of smoke detection systems that may be used in low temperature spaces. The invention also relates to a kit for an air sampling system for a low-temperature space.

2. Discussion of the Related Art

Cold environments, and in particular refrigerated storage facilities, are unique and challenging environments for any smoke detection system. They are characterised by varying low temperatures and frequent traffic flow from workers transporting machinery in and out of the rooms. While most have some form of fast acting automatic doors or plastic barrier curtains to limit warm air ingress, it is inevitable that warm air will enter the room. This constant traffic flow with regular warm air ingress often creates condensation within the rooms and, in situations where the surrounding temperature is below 0 degrees Celsius icing occurs. Icing tends to form on any and all ceiling mounted equipment and structures, generally within close proximity to the entry points.

Smoke detection systems in refrigerated storage facilities are known. Aspirating smoke detection systems generally have a sampling pipe network with a number of sampling points to draw sampling air for testing. These sampling points are generally positioned on the ceiling or walls of the refrigerated space. However, over time, with warm air ingress, the sampling points and associated pipes can become blocked with ice. This causes air flow issues and inoperative detection of smoke.

The maintenance required to rectify this problem (i.e. unblocking of holes or pipes) can be very costly. In some instances, the simplest known solution is to remove the section of pipe closest to the sampling point and fit a new pipe section. In addition, access to equipment within the refrigerated storage facility may become inconvenient during repairs.

Similar problems exist for air sampling systems for other low-temperature environments, such as cold outdoor environments. Some of the condensation related problems begin to arise at temperatures about 4 degrees Celsius (or possibly higher if certain conditions exist), and typically get worse as the temperature drops down to, or below the freezing point of water, 0 degrees Celsius. It is therefore an object of the present invention to provide an air sampling system and a kit for an air sampling system which overcomes or at least ameliorates one of the abovementioned problems associated with low-temperature environments, especially refrigerated environments.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In accordance with a first aspect of the present invention there is provided, an air sampling system for a low-temperature space, the air sampling system including: an air sampling pipe for passing sampling air to an air sampling device; a sampling conduit extending from an entry port from the low-temperature space to outside the low-temperature space; the sampling conduit being connected to the sampling pipe, wherein the sampling conduit is selectively accessible from outside the low-temperature space for removal of ice build up within the sampling conduit.

The sampling conduit is preferably a straight length of conduit of sufficient length to extend through a partition, wall or ceiling defining a boundary of the low-temperature space, as the case may be. Thus, the conduit has an entry port within the low-temperature space and an exit port external to the low-temperature space. The entry port may be "within" the low-temperature space by being at the boundary of the low-temperature space, for example by being a hole in the partition that faces the low-temperature space.

The access to the sampling conduit is preferably in line with the longitudinal axis of the sampling conduit to enable line-of-sight visual inspection and also to enable the insertion of a rod or similar instrument to remove ice build up, which typically occurs at the entry port of the sampling conduit inside the low-temperature space, i.e. at the sampling point. For this reason, the entry port of the sampling conduit is preferably at least the same dimension (in terms of cross-section) as the access opening. Typically, for ease of construction and cleaning-access, the sampling conduit will have a continuous cross-section. Another feature is a bell or dome shaped nozzle at the entry port of the sampling conduit. Typically the sampling conduit is formed of cylindrical pipe, preferably plastic and typically of about 25 mm in diameter. The entry port may be coated with silicone to prevent ice build up. Insulation of the sampling conduit is also possible. The sampling conduit may be a one-piece construction but this need not be the case.

Preferably, the air sampling system includes a restrictor, such as a small entry port or restriction fitting, which is outside the low-temperature space. Most preferably the restrictor is positioned proximate an end of the sampling conduit, or downstream thereof. In some cases the restrictor may be located in or near the sampling pipe.

The sampling conduit may be selectively accessible from outside the low-temperature space through the use of an access opening. This may be in the form of an access hatch such as a sliding or hinged closure. Preferably any such access hatch has a self-closing feature.

In one form of the invention, the sampling conduit is connected to the sampling pipe with an access opening formed therein. In a preferred form of the invention, the sampling pipe connects to an exit port on the outside of the sampling conduit by means of a connection assembly on the downstream end of the sampling conduit such that the connection assembly which is selectively removable from the exit port of the sampling conduit. In this embodiment, it will be understood that the sampling pipe may have a number of connection assemblies and sampling conduits arranged at spaced intervals along the sampling pipe to draw air from the low-temperature space at a number of respective spaced sampling points. The invention may include more than one sampling pipe. For example, there may be a sampling pipe network arranged in spaced rows, establishing a grid pattern of sampling points within the low-temperature space.

The selectively removable connection assembly may be or include a flexible connector pipe. The connection assembly preferably either additionally or alternatively includes a fitting, such as an adaptor, union or T-piece, that fits to the sampling pipe and also joins directly or indirectly to the sampling conduit. The connection assembly has a restriction fitting at a mating portion or end which is connectable with the exit port of the sampling conduit and selectively removable therefrom. The restriction fitting may be defined by a separate or separable end piece of the connection assembly or may be integrally formed with the connection assembly.

The restriction fitting of the connection assembly includes a restrictor, for example in the form of a small entry port, for sampling air and defining the flow rate from the low-temperature space, through the sampling conduit, to the sampling pipe. The restrictor may be located at an end of the restriction fitting which mates with the sampling conduit. For example, the restrictor may be comprised of a hole or holes forming a small entry port at the end of the restriction fitting, whereby the end is closed but for the hole(s). Alternatively, the restrictor may be downstream from the end of the connection assembly that mates with the sampling conduit. In either case, it will be understood that the restrictor is selectively removable with the connection assembly from the sampling conduit, enabling access to the full cross-section of the sampling conduit to allow for cleaning of the conduit by pushing debris and/or ice through the upstream end of the sampling conduit, i.e. the end that faces the low-temperature space.

The sampling conduit is preferably shaped so that the cross section of the sampling conduit's duct remains substantially constant (or increases rather than decreases) from its downstream end to its upstream end, so that the ice or debris does not clog at its upstream end when pushed through the sampling conduit during cleaning.

It is appreciated that since the restrictor forms part of the connection assembly, the restrictor may be easily inspected and, if necessary, cleaned or replaced. This is in contrast with arrangements in which the restrictor is integral to the sampling conduit or only is accessible only from within the low-temperature space (e.g. by forming at least part of the sampling hole in the low-temperature space).

It is also appreciated that the restrictor may be a collection of apertures, rather than a single aperture, forming the small entry port. The restrictor may cause restriction, at least in part, by increasing turbulent flow in comparison with flow either side of the restrictor.

The restriction fitting may include one or more apertures which are closable when the connection assembly is assembled correctly to the sampling conduit. Preferably these apertures are large in comparison to the small entry port. The relatively large apertures which are closed when the connection assembly and sampling conduit are properly reassembled, enable detection of mis-assembly of the connection assembly with the sampling conduit. If the connection assembly and the sampling conduit are not properly reassembled then the apertures simulate a broken pipe condition which should trigger an urgent flow fault in the air sampling device, e.g. the smoke detector unit. This safeguards against inadvertent removal of the connection assembly from the sampling conduit, improper reassembly or simply the act of forgetting to reassemble the sampling conduit with the connection assembly.

In a preferred form of the invention, the one or more large apertures are formed in the side wall of the restriction fitting, being closed by contact with the inside of the side wall of the sampling conduit. Preferably, there are two diametrically opposed apertures. The apertures may be round although other shapes are possible.

In one embodiment, the restriction fitting also includes a flanged end opposite the closed end of the connection assembly. This preferably acts as a stop for insertion of the connection assembly into the sampling conduit, to ensure that the connection assembly and sampling conduit are correctly reassembled.

In one form of the invention, the restriction fitting includes a fitting portion that is formed by any union or coupling part or assembly for joining one pipe to another. However, preferably, the fitting portion has a first component that seals with the sampling conduit, a second component that seals with either a sampling pipe or a component such as a connector pipe that is in fluid communication with the sampling pipe. The restriction fitting also includes a fastening component that seals together the first and second components. Preferably the fastening is by a threaded connection to one of the first and second components. Preferably the seal between the first and second components is provided by at least one O-ring, gasket etc. that is between the first and second components.

Preferably, the restrictor is integral to or held by the fitting portion. Preferably, the restrictor acts as to limit flow through the sampling conduit to a pre-determined flow-rate. Preferably the restrictor is held between the first component and the second component when the fitting portion is assembled. In one embodiment the restrictor is a flow-restricting washer or orifice-plate, which preferably has an inner diameter that is less than the inner diameter of the sampling conduit and of the connection assembly downstream and upstream from the restrictor.

In accordance with a second aspect of the present invention there is provided air sampling system for a low-temperature space, the air sampling system including: an air sampling pipe for passing sampling air to an air sampling device; a sampling conduit extending from the low-temperature space to outside of the low-temperature space, the sampling conduit being connectable to the sampling pipe through a connection assembly which is removably connectable with an exit port of the sampling conduit, outside of the low-temperature space, wherein the removable connection assembly includes: (i) a restrictor for restricting flow of sampling air, the restrictor having a first characteristic flow-impedance, and (ii) a passageway between the restrictor and the sampling pipe, wherein the passageway has a second characteristic flow-impedance that is less than the first characteristic flow impedance.

Preferably, the location of the restrictor in a removable connection assembly facilitates inspection and any necessary clearing of the small entry port. Any of the other features described above in connection with the first aspect of the invention may also be applied. For example, the removable connection assembly may include one or more relatively larger apertures and/or a flanged end opposite the substantially closed end. The connection assembly may include a connector pipe extending between the air sampling pipe and the sampling conduit. In another embodiment, the connection assembly may directly connect the sampling conduit to the sampling pipe, without including an intermediate connector pipe.

In a third aspect of the present invention there is provided an air sampling system for a low-temperature space, the air sampling system including: an air sampling pipe for passing sampling air to an air sampling device; a sampling conduit extending from the low-temperature space to outside of the low-temperature space, the sampling conduit being connectable to the sampling pipe through a connection assembly which is removably connectable with an exit port of the sampling conduit, outside of the low-temperature space, wherein the removable connection assembly includes: (i) a restrictor having an opening having a first cross-sectional area for restricting flow of sampling air, and (ii) a passageway between the restrictor and the sampling pipe, wherein the passageway has a minimum cross-sectional area that is greater than the first cross-sectional area.

In accordance with a fourth aspect of the present invention, there is provided an air sampling system for a low-temperature space, the air sampling system including:

an air sampling pipe that runs outside the low-temperature space for passing sampling air to an air sampling device, wherein when the sampled air is in the sampling pipe the sampled air is above a temperature that is above the freezing point of water and also above the temperature of the low-temperature space; and a sampling conduit extending from the low-temperature space to the sampling pipe, for collecting air sample from the low-temperature space;

a restrictor having a characteristic flow impedance for determining a flow-rate of the sampled air through the sampling conduit, wherein the restrictor is situated between the low-temperature space and the sampling pipe, at a location sufficiently warm to prevent water vapour from causing a temperature-related blockage at the restrictor.

In one embodiment the restrictor is part of the sampling conduit. In another embodiment the air sampling system further includes a connection assembly that connects the sampling conduit to the sampling pipe, wherein the restrictor is part of the connection assembly. The restrictor may be integrally formed with the sampling conduit or connection assembly.

The temperature-related blocking could be blocking caused by condensation, and especially freezing, of the water vapour on the restrictor.

Preferably for this and all other aspects of the invention, the low-temperature space is a space having a temperature of +4 degrees Celsius or below. Such a low-temperature space may advantageously be a refrigerated space, preferably enclosed by surrounding walls, a floor and a ceiling.

In the case of the low-temperature space being a refrigerated space, the temperature of the low-temperature space is preferably between −40 degrees Celsius and +4 degrees Celsius, but generally is at or around −25 degrees Celsius. Whereby the low-temperature space is below 0 degrees Celsius, it is preferable for the restrictor to be placed in a warmer environment at a location sufficiently far from the low-temperature space so as to prevent water vapour, sampled from the low-temperature space, from freezing on the restrictor. In one embodiment, the restrictor is situated at least 30 cm from the interior of the refrigerated space. Preferably, the restrictor is situated at least 15 cm, and preferably between 15 and 25 cm, from an outside surface of a wall panel or partition that insulates the low-temperature space. In addition to the flow rate being determined by the characteristic impedance of the flow restrictor, the flow rate may also determined by a pressure controlled by a pump or fan. However, optionally, the characteristic flow impedance of the restrictor may be such that the restrictor acts a flow-limiting device.

In accordance with a fifth aspect of the present invention, there is provided a kit for an air sampling system for a low-temperature space, the kit including: a sampling conduit to extend from the low-temperature space to outside the low-temperature space, the sampling conduit having an entry port and an exit port; and a connection assembly which is removably connectable with the exit port, at least one of the connection assembly and the sampling conduit having one or more apertures which are closable by the side wall(s) of the other of the connection assembly and the sampling conduit when the connection assembly is correctly connected with the sampling conduit.

Any of the features described above in connection with other aspects of the invention may be applied to the fourth aspect of the invention.

In accordance with a sixth aspect of the present invention, there is provided, a kit for an air sampling system for a low-temperature space, the kit including:

a sampling conduit to extend from the low-temperature space to outside the low-temperature space, the sampling conduit having an entry port and an exit port; and a connection assembly which is removably connectable with the exit port for connecting the sampling conduit to a sampling pipe, the connection assembly having: (i) a restrictor for restricting flow of sampling air, the restrictor having a first characteristic flow-impedance, and (ii) a passageway between the restrictor and the sampling pipe, wherein the passageway has a second characteristic flow-impedance that is less than the first characteristic flow impedance.

Preferably, restrictor has an opening having a first cross-sectional area for determining first characteristic impedance and the passageway has a minimum cross-sectional area that is greater than the first cross-sectional area, so that the second characteristic impedance is less than the first characteristic impedance In one embodiment the restrictor is a substantially closed end of the connection assembly that has a small entry port for sampling air.

In a seventh aspect of the present invention, there is provided a kit for an air sampling system for a low-temperature space, the kit including:

a sampling conduit to extend from the low-temperature space to outside the low-temperature space, the sampling conduit having an entry port and an exit port; and a connection assembly which is removably connectable with the exit port for connecting the sampling conduit to a sampling pipe, the connection assembly having: (i) a restrictor having an opening having a first cross-sectional area for restricting flow of sampling air, and (ii) a passageway between the restrictor and the sampling pipe, wherein the passageway has a minimum cross-sectional area that is greater than the first cross-sectional area.

It will be appreciated that any of the first to seventh aspects of the invention may also include a mounting system for mounting the sampling conduit through a side wall, floor or ceiling that insulates the refrigerated space.

In an eighth aspect of the present invention, there is provided a method of evaluating assembly of an air sampling network in an network portion between (a) a sampling point for sampling air from a space being or to be monitored by an air sampling device, and (b) a sampling pipe outside the space, wherein the method comprises:

measuring a flow parameter;

determining, based on the flow parameter, the presence or absence of a flow restrictor component of the network portion; and indicating a condition of assembly based on the determined presence or absence of the flow restrictor.

Preferably, the sampling device is a particle detector.

Preferably, when the measured flow parameter is above a predetermined threshold, the method determines a fault condition. In one embodiment, the predetermined threshold is between a first flow rate that is normal for the network portion being correctly assembled, and a second flow rate that is expected for the network being assembled without the flow restrictor component. In another embodiment, the predetermined threshold is between a first flow rate that is normal for the network portion being correctly assembled, and a second flow rate that is expected when the sampling point is disconnected from the sampling pipe.

In one embodiment, the method evaluates the assembly between (a) the sampling pipe, the sampling pipe being configured for passing air from the connection assembly toward the particle detector, and (b) an exit port of a sampling conduit, the sampling conduit being configured for passing air from the monitored space to the connection assembly, wherein in correct assembly of the sampling network, the flow restrictor component forms part of the connection assembly.

Preferably, the method includes comparing a measured flow parameter with a threshold flow value that is selected to be greater than an expected rate when the restrictor is connected. In one embodiment, the threshold flow value is additionally selected to be less than an expected flow rate when the air sampling pipe and sampling conduit are connected, but without a restrictor in the connection.

Advantageously, this provides the method with a sensitivity to detect that the connection has been made but that the restrictor is absent. The threshold may be derived empirically or may be calculated from the known characteristic flow-impedances of the respective sampling conduit, restrictor and sampling pipe.

Preferably, the connection is provided by a connection assembly in accordance with any of the other aspects of the invention.

As would be understood by a person skilled in the art, the characteristic flow impedance of the restrictor is preferably selected to be greater than the characteristic impedance of the sampling conduit and all portions of the connection assembly other than at the restrictor. In this manner, it is easy to measure the restrictor's effect on the overall impendence of the sampling conduit and connection assembly, and the consequential sample air flow.

In a ninth aspect of the present invention, there is provided a computing system having: a memory for storing a set of instructions that are executable by a processing system; and a processing system configured to read and execute the instructions, wherein upon executing the instructions the computing system performs the method according to the eighth aspect of the present invention. Preferably the flow sensor is an ultrasonic flow sensor, but other types of flow sensors may be used, e.g. a thermal flow sensor, an anemometer or the like.

In a tenth aspect of the present invention, there is provided an air sampling device having a computing system in accordance with the ninth aspect of the present invention.

Preferably, the air sampling device is (or includes) a particle detector, more preferably a smoke detector.

In an eleventh aspect of the present invention there is provided an air monitoring system, having and an air sampling system in accordance with any one of the first, second, third or fourth aspects of the present invention, wherein the air sampling system feeds into said sampling device. Preferably the particle detector is a particle detector in accordance with the tenth aspect of the present invention. Preferably, the air monitoring system is a particle detection system, more preferably a smoke detection system.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

In order that the invention may be more fully understood, one embodiment will now be described by way of example, with reference to the figures in which.

DETAILED DESCRIPTION OF THE EMBODIMENTS

The exemplary embodiments of the invention are described hereinafter with reference to use for a refrigerated space. However, the present invention may alternatively be applied to other low-temperature environments, such as cold outdoor environments.

The exemplary embodiments are also described with reference to a particle detection system in which monitoring of sampled air is performed by an air sampling device that is a particle detector. However, the air monitoring system or sampling device may additionally or alternatively be adapted to analyse and/or detect other characteristics or components of the air. For example the air monitoring system or sampling device may be a gas detector or other device capable of detecting the presence and or concentration of one or more target gasses. An example of such an air sampling device is sold by Xtralis Technologies Ltd under the product name Vesda Eco.

Figure 1:
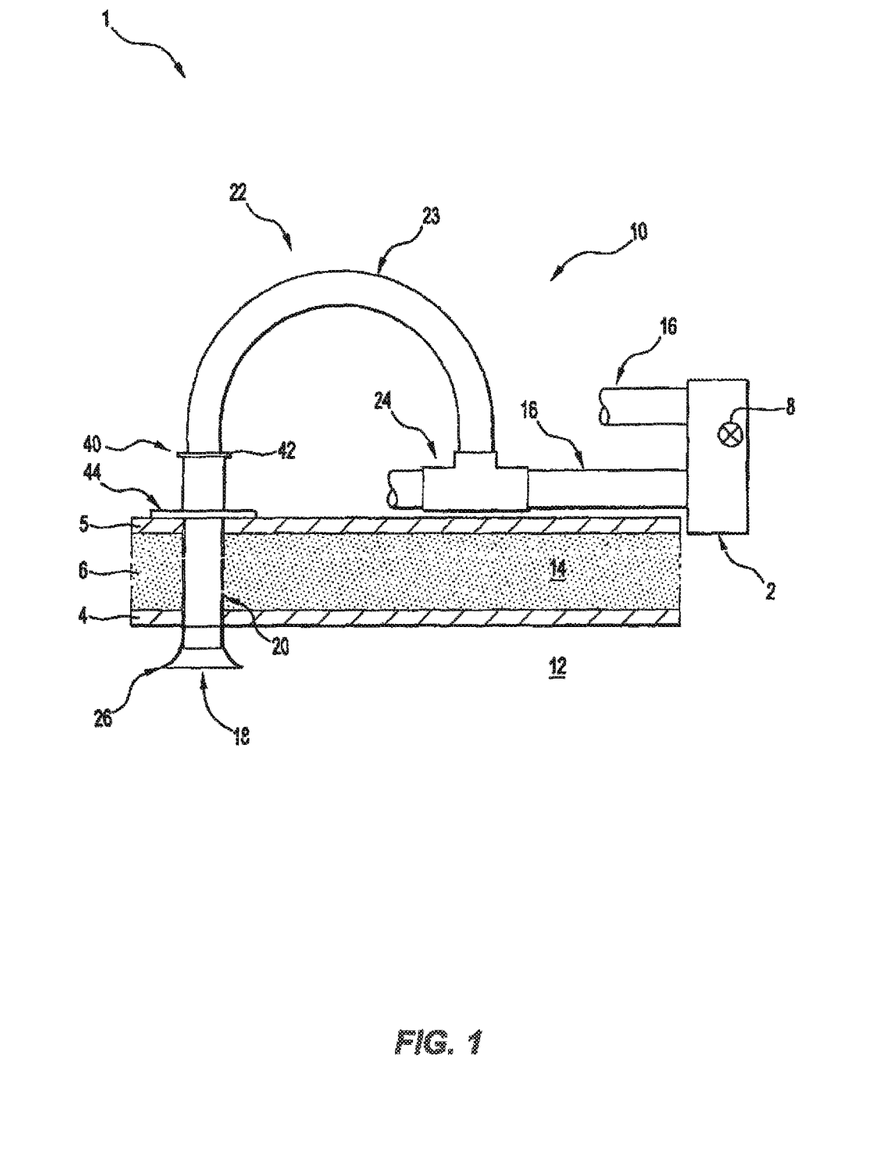
FIG. 1 is a schematic illustration of a particle detection system having an air sampling system according to an embodiment of the present invention.

FIG. 1 illustrates an air monitoring system in the form of a particle detection system 1 for a refrigerated space 12. The refrigerated space 12 is typically enclosed by a floor, walls and a ceiling including ceiling panel 14. The ceiling and the walls may be insulating partitions or of an insulated sandwiched construction, as is known in the prior art. Typically, however, the sandwiched construction includes internal and external metallic panels 4 and 5, respectively, with foam insulation 6 between the metallic panels 4, 5.

The particle detection system 1 includes a particle detector 2 in the form of an aspirating smoke detector, and an air sampling system 10 for drawing air from the refrigerated space 12. Thus, externally of the refrigerated space 12 is a network of sampling pipes 16, two of which are shown in FIG. 1. The sampling pipes connect to a sampling device—in this case, the aspirating smoke detector 2—above the ceiling panel 14. The sampling pipes 16 run along the outside of the refrigerated space 12 to connect to the sampling device 2, either directly or via a manifold (not shown) proximate the sampling device 2. A fan 8 may be provided within the aspirating smoke detector unit or elsewhere in the sample pipe network to draw air from the refrigerated space 12, through the sampling system 10, to the smoke detector 2. Additionally, it is also possible for the outlet of the smoke detector unit to feed back into the refrigerated space 12 to create a closed loop system (not shown) to avoid the introduction of warm and humid air into the refrigerated space 12 when the detector unit is powered down for any reason.

Each sampling pipe 16 may include a number of sampling points 18 at spaced locations within the refrigerated space 12. Each of the sampling points exists at an entry port of a corresponding sampling conduit 20 which is connected to the sampling pipe 16 by means of a connector assembly 22. The connection assembly 22 includes a flexible connector pipe 23 intermediate a restriction fitting 40, that fits to the sampling conduit 20, and a T-junction fitting 24 that fits to the sampling pipe 16. Thus, the connection assembly forms a branch that stems from the sampling pipe, the branch including the sampling conduit.

There may be a number of such T-junctions 24 along a single length of sampling pipe 16, thereby providing a number of sample points 18 along a single length of sampling pipe 16. Furthermore, it will be appreciated that a number of lengths of sampling pipe 16 can be arranged side by side to create a grid (or other geometry) of sampling points 18.

The sampling conduit 20 is of a sufficient length to extend across the width of the ceiling panel 14 or a wall panel, as the case may be. The sampling conduit 20 extends from the inside of the refrigerated space to outside the refrigerated space as most clearly illustrated in FIGS. 2 and 3. As shown in FIG. 1, the inside end (entry port) of the sampling conduit 20 may be provided with a bell-shaped sample nozzle 26.

Figure 3:
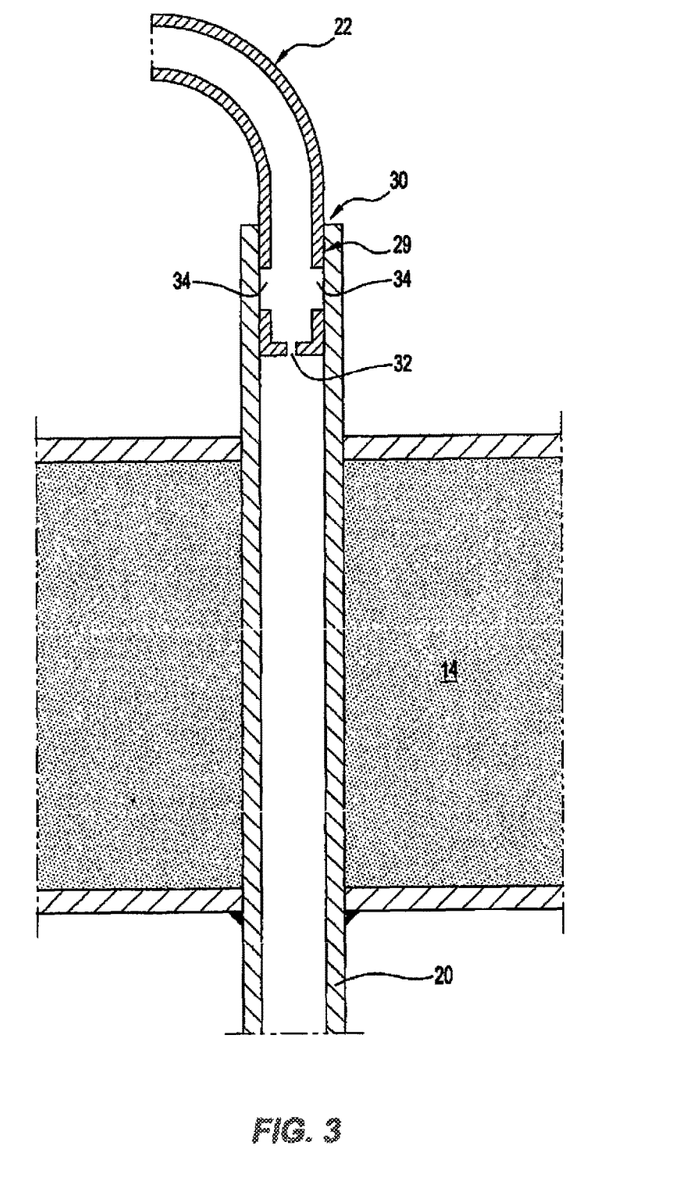
FIG. 3 is a detail of an alternative embodiment of the air sampling system illustrated in FIG. 1.
Figure 4:
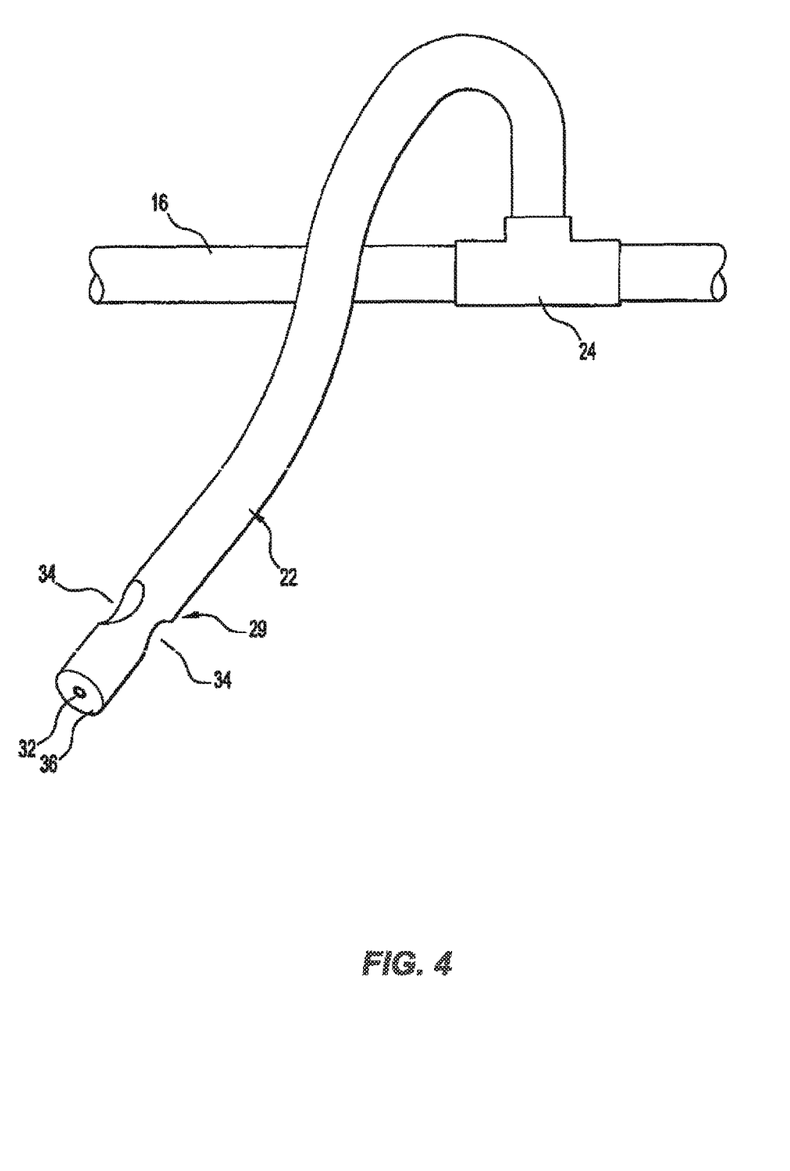
FIG. 4 is a perspective view of another part of the air sampling system of FIG. 1, corresponding to the view shown in FIG. 3.

At the other end of the sampling conduit 20, the connection assembly 22 is received in the exit port 30 of the sampling conduit 20. In FIGS. 3 and 4, the flexible connection assembly 22 has an integral end construction, such that the end portion 29 of the flexible connector pipe 23 acts like the restriction fitting 40. The restriction fitting 29 in this embodiment includes a small entry port 32, to restrict sample flow, and two relatively larger side apertures 34. The small entry port 32 is disposed in a central location in a substantially closed end 36 of the restriction fitting 29. The two larger apertures 34 are disposed in the side walls of the restriction fitting 29. As will be understood from FIG. 3, when the end of the restriction fitting 29 is inserted correctly into the exit port 30 of the sampling conduit 20, the large apertures 34 will be closed by sealing against the inside surface of the wall of the sampling conduit 20. However, as will be understood from FIG. 4, if the restriction fitting 29 of the connection assembly 22 is not properly inserted back into the sampling conduit 20 then the large apertures 34 are able to draw in a large quantity of air, sufficient to trigger a fault within the detector unit 2.

Preferably the leakage through the large apertures 34 approximates the leakage of a broken pipe. Thus, aperture 34 may be of a similar sectional area as the pipe 16.

Figure 2:
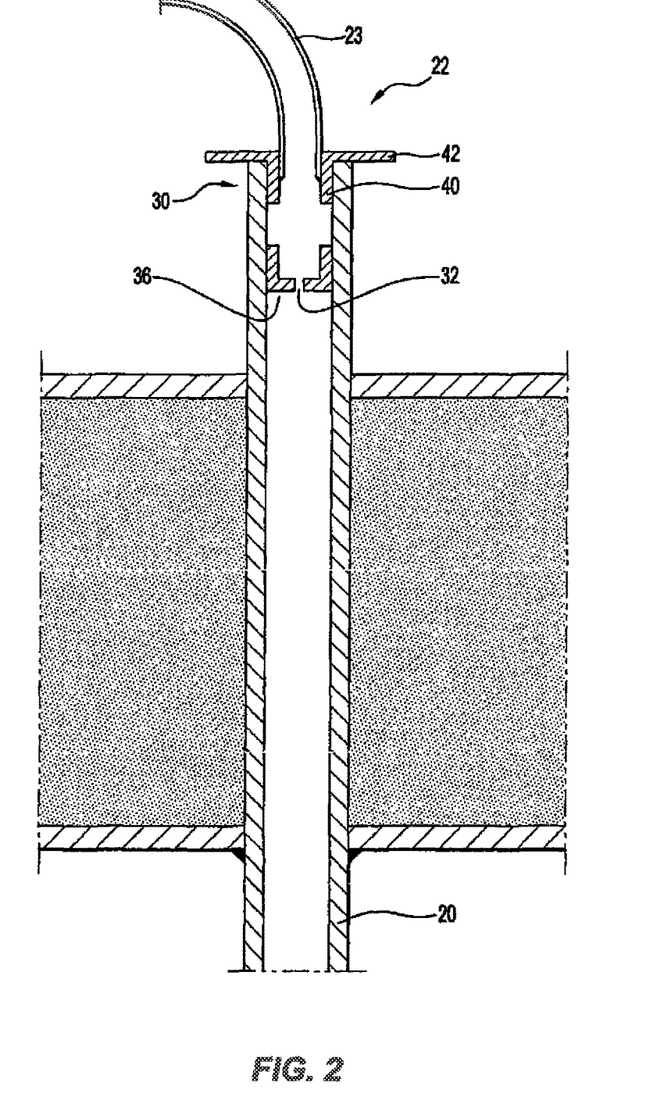
FIG. 2 is a detailed view of part of the air sampling system of FIG. 1.
Figure 5:
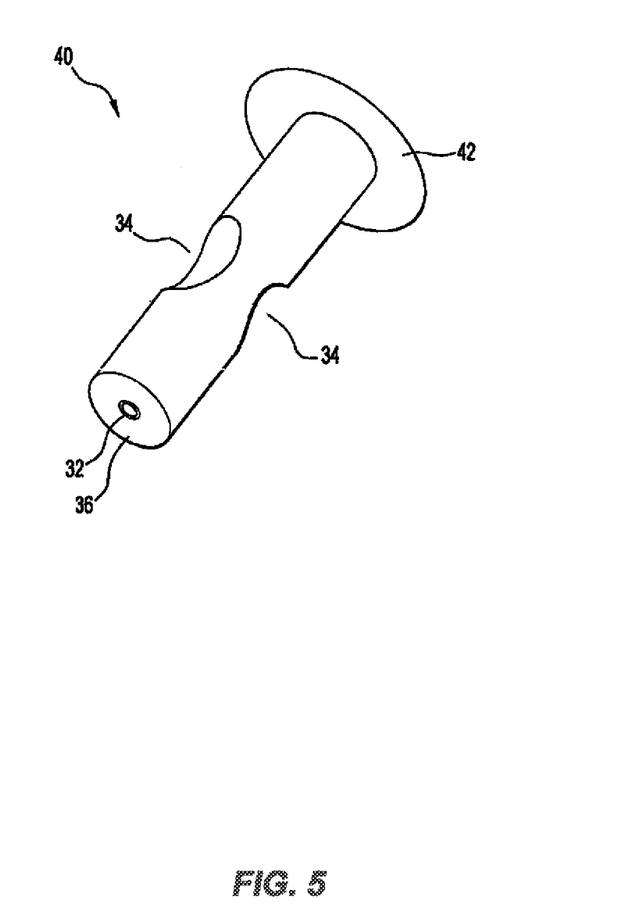
FIG. 5 is a detailed view of an end piece, corresponding to the embodiment illustrated in FIG. 2.

FIGS. 2 and 5 illustrate an alternative embodiment whereby the connection assembly 22 is comprised of multiple component parts which preferably are separable from each other. One of the components is a connector pipe 23. In this embodiment, the connector pipe is advantageously flexible, but it is appreciated that a rigid connector pipe may be used. Attached to one end of the connector pipe 23 is a restriction fitting 40 in the form of an adaptor. The restriction fitting 40 constitutes a second component of the connection assembly 22, and fits the flexible pipe 23 to the sampling conduit 20. Thus, the restriction fitting 40 acts as an end piece of the connection assembly 22. The restriction fitting 40 includes the small entry port 32 at the substantially closed end 36, with two diametrically opposed, relatively larger apertures 34, all of which serve a similar purpose as described above. Additionally, the restriction fitting 40 includes a peripheral flange 42 which serves to locate the restriction fitting 40 in its properly installed position within the sampling conduit 20. The restriction fitting 40, including the flange 42, peripheral side wall and substantially closed end 36 is preferably of one piece, integral construction. The restriction fitting 40 may be an integrally moulded piece. It will be appreciated that the provision of a separate restriction fitting 40 is a simpler construction than machining or forming the small entry port 32 and apertures 34 into the end of a flexible pipe 22.

Figure 6:
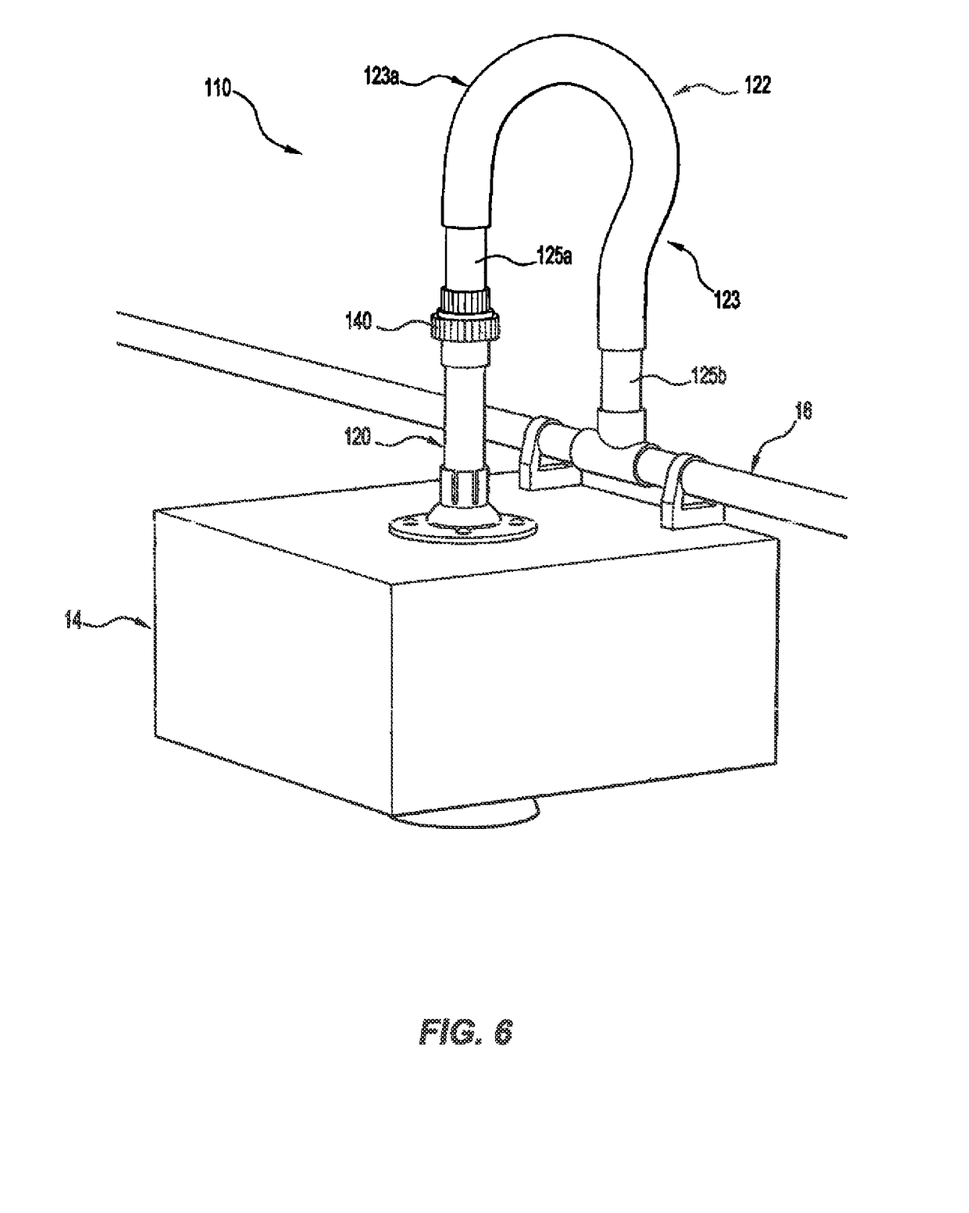
FIG. 6 is an illustration of a portion of an air sampling system in accordance with another embodiment of the present invention.

An embodiment of an alternative air sampling system 110 is illustrated in FIG. 6. The air sampling system 110 uses an alternative connection assembly 122 which is similar to, and may be used interchangeably with, the connection assembly 22 in air sampling system 10. In this embodiment, the connector pipe 123 includes a flexible pipe segment 123a terminated with upstream and downstream rigid pipe pieces 125a and 125b, respectively. It is, however, appreciated, that the pipe 123 may be interchanged with a pipe that is either flexible or rigid across its entire length or for any portion thereof, as desired. Connection assembly 122 includes an alternative restriction fitting 140 for fitting the connection assembly 122 to the sampling conduit 120.

Figure 7:
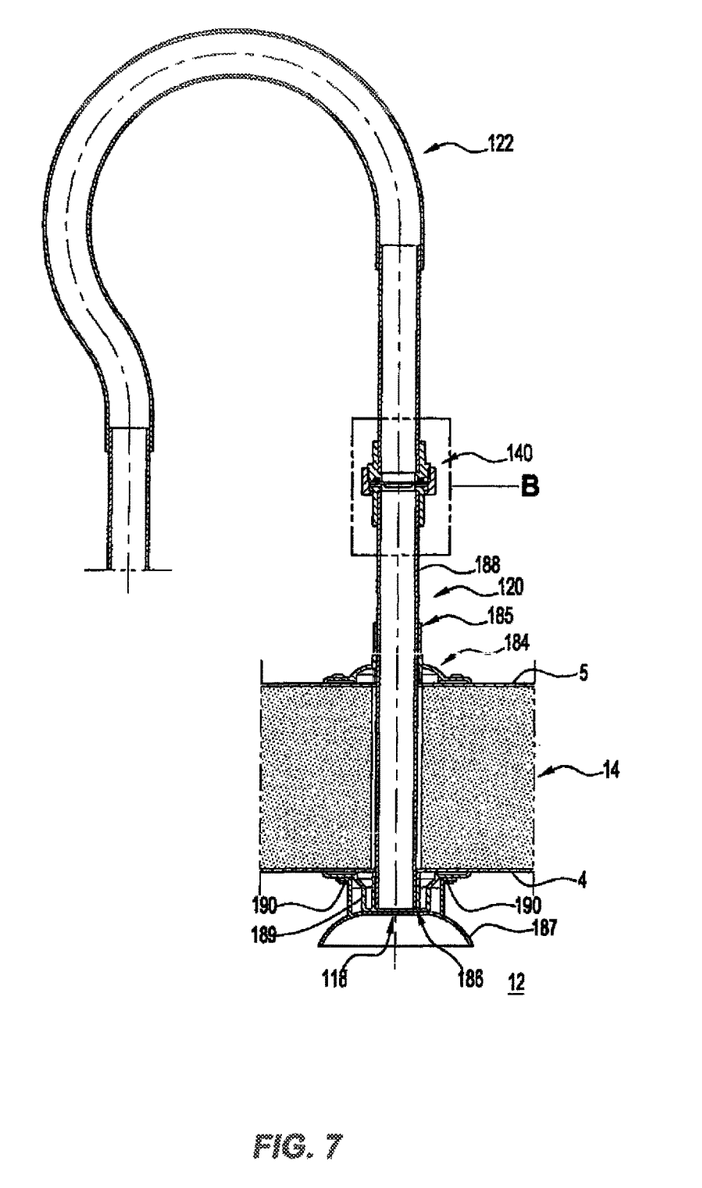
FIG. 7 is a longitudinal sectional view through the air sampling system illustrated in FIG. 6.

FIG. 7 illustrates a longitudinal sectional view through the connection assembly 122 and sampling conduit 120. The connection assembly 122 may alternatively be attached to the sampling conduit 20 of FIGS. 1 to 3.

Figure 8:
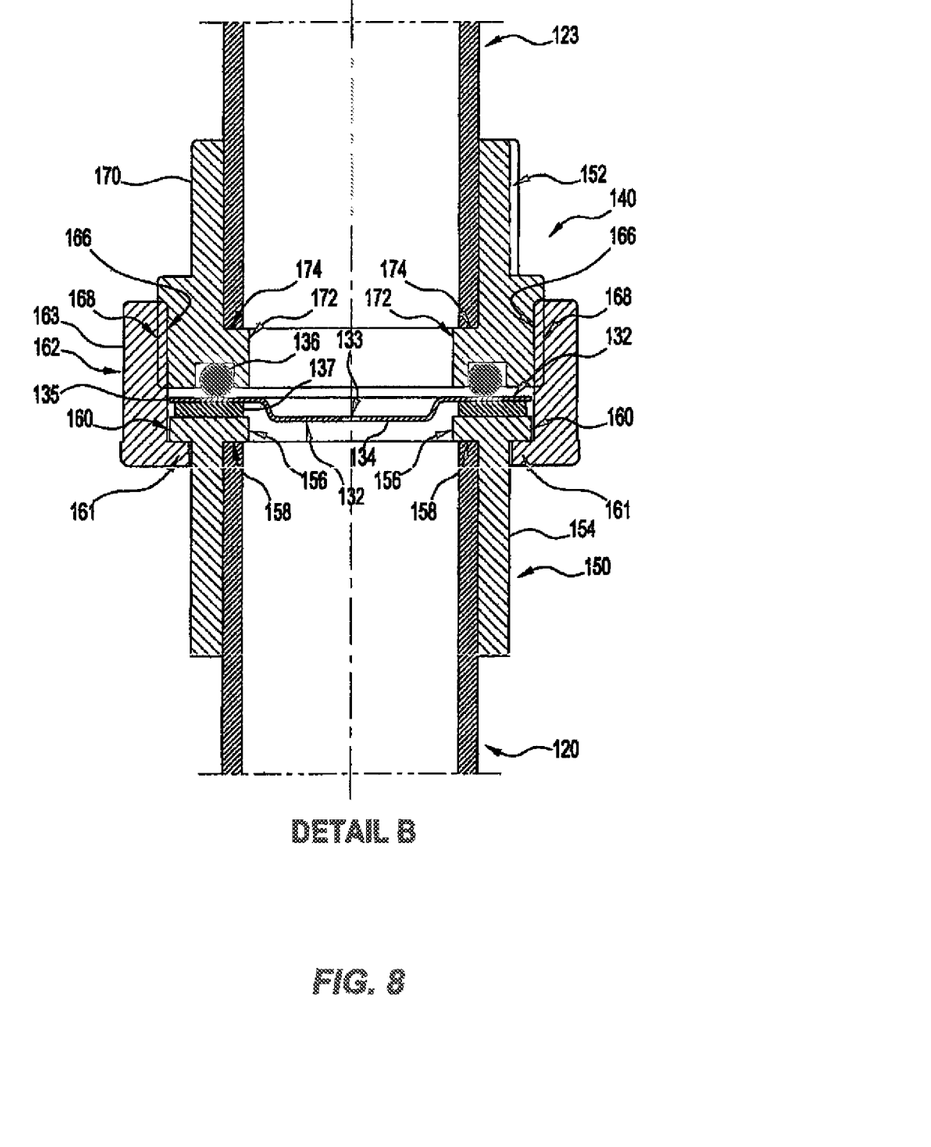
FIG. 8 is an enlarged view of a restriction fitting illustrated in the air sampling system of FIGS. 6 and 7.

An enlarged view of the restriction fitting 140 joined to the sampling conduit 120 and connector pipe 123 is illustrated in FIG. 8. Restriction fitting 140 includes a fitting portion in the form of a union fitting having a first component 150, which is in this case configured to seal with the sampling conduit 120, and a second component 152, which is in this case configured to seal with a connector pipe 123. It is appreciated, however, that the orientation of the restriction fitting may be reversed so the first component 150 and second component 152 mate with the connector pipe 123 and sampling conduit 120, respectively.

The first component 150 (in this case the upstream component) includes collar 154 having a tight fit with the sampling conduit 120. The top (downstream end) of the collar has an inner flange 156 for sitting on the edge 158 of the sampling conduit 120. The top of the collar 150 also includes an outward flange 160 for interferingly abutting with a bottom inner flange 161 of a fastening member 162. This prevents the fastening member 162 from being removed from the sampling conduit 129 when the first component 150 is attached to the sampling conduit 120. Extending upwardly from the fastening member's inner flange 161 is a fastening ring 163 having an inner thread 166, which can be screwed onto thread 168 on the bottom outside surface of the second component 152 to tighten the second component 152 towards the first component 150 and to create a seal therebetween. The second component has an inner flange collar 170 having a tight fit with the connector pipe 123 and an inner flange 172 to sit beneath and abut the bottom edge 174 of the connector pipe 123.

Between the first and second components 150, 152 is a restrictor 132 in the form of an orifice plate. However, the restrictor 132 is also shaped to fit on the sampling conduit in a self-locating manner. This is achieved by a central portion 134 of the restrictor 132 being sunken from the restrictor's periphery 135. In this embodiment the restrictor is metallic, but in other embodiments non-metallic materials, such as plastic or rubber, may be used.

A seal is created between the first and second components 150, 152 by a rubber O-ring seals 136 and a ring-shaped self-adhesive foam seal 137 on the respective sides of the restrictor 132. This creates seals between the first component 150 and the restrictor 132, and between the restrictor 132 and the second component 152.

The restrictor has an inner diameter (i.e. the diameter of the O-ring hole 133) which is less than the inner diameter of the downstream flow path to the sampling pipe 16. Thus, the diameter of hole 133 is less than the inner diameter of the second component 152 and also less than the inner diameter of the connector pipe 123. The diameter of hole 133 is similarly less than the inner diameter of the entire sampling conduit (including the sampling point at the end of the sampling conduit). The precise diameter of the hole 133 is selected to provide a desired flow-restriction that is dictated by the dimensions and configuration of the sampling system 10 and detector 2, and the characteristics of the fan 8. The diameter can be determined in any known fashion including using software that has been specialised for this purpose, such as Xtralis Technologies Ltd's VESDA ASPIRE2 pipe network design software. Typically, the hole has a diameter of between 2 mm and 10 mm. As would be appreciated by a person skilled in the art, restrictor 132 may allow restrictive flow of air by having a plurality of holes, rather than a single hole 132. In this case, the combined cross section of all the restrictor's holes is the same as cross section of the single hole 132. By comparison the respective minimum (and in this case constant) inside diameters of the sampling conduit and connector pipe are both 25 mm.

By this design, the characteristic flow-impedance of the restrictor 132 dominates the overall impedance to flow of air sampled from the refrigerated space to the sampling pipe 16. Accordingly, if the restrictor 132 is absent (for example if the sampling system 110 is not correctly assembled), there will be an increase in flow rate through the sampling network 110. The flow rate is measured by a flow-rate meter having a transducer (not shown) either at the particle detector 2 or elsewhere in the sampling system 110. In one arrangement, the flow is measured in either the sampling conduit 120 or the connection assembly 122, but preferably at a downstream end of the connection assembly. Alternatively, an accurate measurement can be acquired by including flow measurement transducers in the sampling pipe 16, upstream and downstream from the sampling conduit 122. The difference in flow between the two transducer measurements is attributable to the flow through the sampling conduit 120 and connection assembly 122. In this embodiment, flow is measured by an ultrasonic transducer, but in other embodiments other types of flow sensor may be used, e.g. a thermal flow sensor.

It is appreciated that part of the restriction fitting may be integrally formed or permanently connected with the sampling conduit 120. However, the restrictor component 133 should preferably, even in this case, still be removable (or at least displaceable) from the sampling conduit 120, so as to provide good access to the sampling conduit for cleaning. To account for such variations, as used herein the term "sampling conduit" is intended to mean the part of the sampling network from the refrigerated space up to, but not including, the restrictor. The restrictor itself is part of the "restriction fitting", which is a separate integer from the sampling conduit, even in cases where the sampling conduit 120 includes a portion, part or parts which interact with the restrictor to enable its removal, displacement, placement or fastening.

Figure 9:
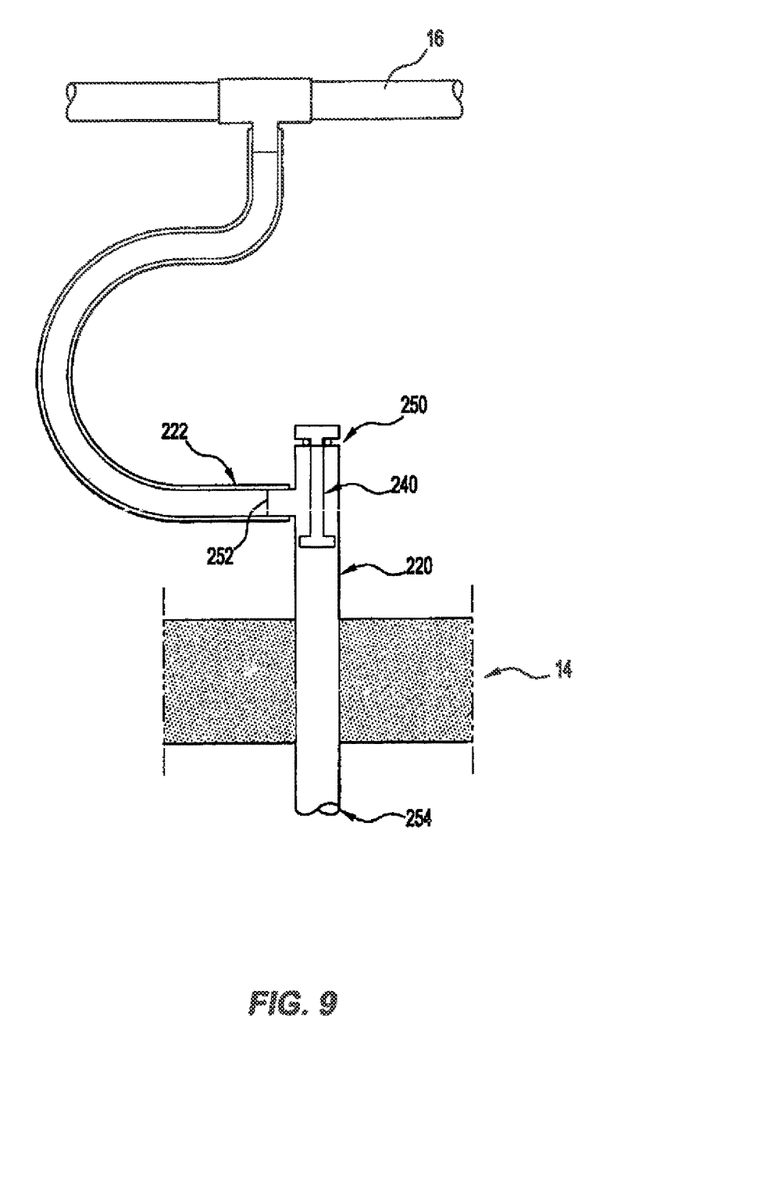
FIG. 9 is a schematic illustration of an air sampling system according to another embodiment of the present invention.

In another embodiment of the invention, or as an additional feature of the embodiments hereinbefore described, the restrictor is positioned in the sampling network at a location sufficiently downstream from the sampling point so as to be at a temperature above the freezing point of water, i.e. above 0 degrees Celsius. In such an arrangement, it is not necessary that the restrictor be part of the connection assembly. An embodiment of such an arrangement is illustrated in FIG. 9, which shows restrictor fitting 240 being removable from a first opening 250 in the sampling conduit 220. The sampling conduit has a second opening 252 which forms the sampling conduit's output to the sampling pipe, and fluidly connects to the connection assembly 222. The restriction fitting restricts the sample flow between the sampling point 254 of the conduit 222 and the output at the second opening 252.

It is appreciated that the restriction fitting 250 may alternatively be located at other locations between the sampling conduit's sampling point 254 and output 252. While it is advantageous for the restriction fitting 250 to be removable from the sampling conduit 220, in some embodiments a restrictor is permanently fixed to or integrally formed with the sampling conduit 220. The placement of the restrictor is nonetheless advantageous by being placed at a location where the sampled air (and the temperature of the sampling conduit) has sufficiently been warmed by the ambient environment so as to be above the freezing point of water. Thus the restrictor does not become clogged with ice. This can reduce the need or regularity for servicing of the sampling network.

For embodiments in which the restrictor may be mistakenly omitted during initial assembly of the sampling pipe network, or during reassembly after servicing, a method may be employed to evaluate the assembly. The method comprises measuring a flow parameter and indicating a condition of assembly that is determinant of the presence or absence of the flow restrictor 40, 140, 240 in an evaluated portion of the network. The method evaluates the assembly at the portion of the air sampling network between (a) the sampling point 18, 118, 254 and (b) a sampling pipe 16 outside the space. In the embodiments of FIGS. 1 to 7, the restrictor forms part of a connection assembly between the sampling conduit 20, 120 and the sampling pipe 16. Thus, the method is used to evaluate the assembly of the connection between the sampling conduit 10, 120 and the sampling pipe 16.

Details of various embodiments of the sampling conduit and its mount to the ceiling 14 are now described. FIGS. 7 and 9 illustrate a sampling conduit 120 mounted to ceiling panel 14. The sampling conduit 120 is held on the metal panel 4 on the top side of the ceiling 14 by top flange assembly 184. The flange assembly 184 has upstanding sprung fingers 185 which retain the sampling conduit 120 in position during and after installation. A lower end 186 of sampling conduit 120 defines the sampling point hole 118. The bottom portion the sampling conduit flanges outwardly from the sampling point 118 and then downwardly to form a dome-shaped cover 187 for the sampling point 118. In the illustrated embodiment this bottom portion of the sampling conduit is formed as a separate part from the main pipe 188 of the sampling conduit. This bottom portion or lower flange 187 locks onto mount 189 which is held onto the bottom metal panel 4 of the ceiling 14 by screws 190. During assembly, sealant is placed between the top and bottom flanges and their corresponding ceiling panel to provide an air-tight seal, avoid leakage at each sampling point and thus prevent air leakage from the refrigerated space 12 through the ceiling 14. Similarly, in the embodiment of FIG. 1, the sampling conduit 20 is preferably surrounded by a suitable sealant within the ceiling panel 14 to eliminate leakage. A sealing grommet 44 may also surround the sampling conduit 20 where it exits the ceiling panel 14.

The foregoing describes only exemplary embodiments of the present invention and modifications may be made thereto without departing from the scope of the invention.

We claim:

1. An air sampling system for a low-temperature space, the low-temperature space having a temperature of +4 degrees Celsius or below, the air sampling system including:
    an air sampling pipe for passing sampling air to an air sampling device;
    a sampling conduit having an entry port of a sampling point in the low-temperature space to an exit port outside the low-temperature space; the sampling conduit further having a longitudinal axis that extends from the entry port to the exit port, the air sampling pipe being connected to the exit port of the sampling conduit via a connection assembly having a restrictor for restricting flow of sampling air from the sampling conduit to the sampling pipe; wherein the connection assembly and restrictor are selectively removable from the exit port of the sampling conduit, enabling access in line with the longitudinal axis to a full cross-section of the sampling conduit from outside the low-temperature space whilst the sampling conduit remains in position, thereby to provide line of sight visual inspection from the exit port to the entry port and enable insertion of a rod into the exit port and sampling conduit for removal of ice build-up within the sampling conduit out through the entry port, wherein the sampling system further includes a bell or dome shaped nozzle at the entry port of the sampling conduit.

2. The air sampling system of claim 1, wherein the sampling conduit has a cross-section that is substantially constant, or has a cross-section that increases in size from a downstream end thereof to an upstream end thereof.

3. The air sampling system of claim 1, wherein the restrictor is part of a restriction fitting located at a mating portion or end of the connection assembly, the mating portion or end being connectable with and selectively removable from the exit port of the sampling conduit.

4. The air sampling system according to claim 1, wherein the restrictor is a flow-restricting washer or orifice-plate.

5. The air sampling system according to claim 1, wherein the restrictor acts as to limit flow through the sampling conduit to a pre-determined flow-rate.

6. The air sampling system according to claim 1, wherein the restrictor is at a location that is warmer than and sufficiently far from the low-temperature space to prevent water vapor, sampled from the low-temperature space, from freezing on the restrictor.

7. The air sampling system of claim 1, wherein the entry port is coated with silicone to prevent ice buildup.

8. The air sampling system according to claim 1, wherein the sampling pipe has a plurality of connection assemblies and sampling conduits arranged at spaced intervals along the sampling pipe to draw air from the low-temperature space at a number of respective spaced sampling points.

9. An air sampling system for a low-temperature space, the low-temperature space having a temperature of +4 degrees Celsius or below, the air sampling system including:
    an air sampling pipe for passing sampling air to an air sampling device;
    a sampling conduit extending from an entry port from the low-temperature space to outside the low-temperature space; the air sampling pipe being connected to an exit port of the sampling conduit via a connection assembly that is removable from the exit port, wherein the connection assembly has a restrictor that is selectively removable with the connection assembly from the sampling conduit, enabling access to the full cross-section of the sampling conduit from outside the low-temperature space while the sampling conduit remains in position, thereby to enable removal of ice build-up within the sampling conduit through the entry port;
    wherein the sampling system further includes a bell or dome shaped nozzle at the entry port of the sampling conduit.

* * * * *